(12) United States Patent
Warshakoon et al.

(10) Patent No.: US 6,930,117 B2
(45) Date of Patent: Aug. 16, 2005

(54) N-ALKYL-4-METHYLENEAMINO-3-HYDROXY-2-PYRIDONES

(75) Inventors: Namal Chithranga Warshakoon, Mason, OH (US); Rodney Dean Bush, Mason, OH (US)

(73) Assignee: The Procter & Gamble Company, CIncinnati, OH (US)

( * ) Notice: Subject to any disclaimer, the term of this patent is extended or adjusted under 35 U.S.C. 154(b) by 0 days.

(21) Appl. No.: 10/702,953

(22) Filed: Nov. 6, 2003

(65) Prior Publication Data

US 2004/0097560 A1 May 20, 2004

Related U.S. Application Data

(60) Provisional application No. 60/425,070, filed on Nov. 9, 2002.

(51) Int. Cl.[7] .................. A61K 31/4412; C07D 213/69
(52) U.S. Cl. ...................... 514/348; 514/344; 546/288; 546/296
(58) Field of Search ................ 514/348, 344; 546/288, 296

(56) References Cited

U.S. PATENT DOCUMENTS

| 385,390 | A | 12/1888 | Shone et al. |
| 5,358,949 | A | 10/1994 | Tabusa et al. |
| 5,407,948 | A | 4/1995 | Fey et al. |
| 5,849,587 | A | 12/1998 | Hanauske-Abel et al. |
| 6,046,219 | A | 4/2000 | Hanauske-Abel et al. |
| 6,080,766 | A | 6/2000 | Hanauske-Abel et al. |

OTHER PUBLICATIONS

Muellner, F.W. et al., "The Synthesis of 1,4–ethano–1,2,3,4–tetrahydroisoquinolines as rigid analogues of adrenergic agents", *J. of Heterocyclic Chemistry*, 1983, vol. 20 pp. 1581–1584.

*Primary Examiner*—Patricia L. Morris
(74) *Attorney, Agent, or Firm*—Naishadh N. Desai; David V. Upite

(57) ABSTRACT

Compounds of Formula (I)

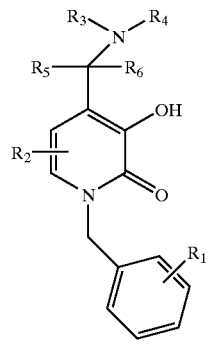

are effective in the treatment of a microbial infection.

6 Claims, No Drawings

N-ALKYL-4-METHYLENEAMINO-3-HYDROXY-2-PYRIDONES

CROSS REFERENCE TO RELATED APPLICATIONS

This application claims priority under Title 35, United States Code 119(e) from U.S. Provisional Application Ser. No. 60/425,070 filed Nov. 9, 2002, incorporated herein by reference.

FIELD OF INVENTION

The invention is directed certain N-alkyl-4-methyleneamino-3-hydroxy-2-pyridones useful as antimicrobials.

BACKGROUND OF INVENTION

The chemical and medical literature describes compounds that are said to be antimicrobial, i.e., capable of destroying or suppressing the growth or reproduction of microorganisms, such as bacteria. For example, such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981).

The mechanism of action of these antibacterials vary. One notable mechanism is bacterial aminopeptidase (bMAP) inhibitors. bMAP inhibition is an important therapeutic target in anti-infective focus area because it is involved in translation of mature proteins, and is conserved among know pathogenic bacteria. Therefore, inhibition of this enzyme would lead to broad spectrum antimicrobial agents.

Many attempts to produce improved antimicrobials yield equivocal results. Indeed, few antimicrobials are produced that are truly clinically-acceptable in term of their spectrum of antimicrobial activity, avoidance of microbial resistance, and pharmacology. Thus there is a continuing need for broad-spectrum antimicrobials, which are effective against resistant microbes.

SUMMARY OF INVENTION

The invention provides compounds which are potent inhibitors of bMAP and which are effective in treating microbial infections. In particular, the present invention relates to compounds having a structure according to the following Formula (I):

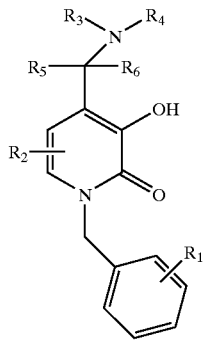
(I)

Another aspect of the invention is directed to methods of using the compounds of Formula (I) for treating a microbial infection in a subject in need thereof.

Another aspect provide for methods of making compounds of Formula (I).

All documents cited are, in relevant part, incorporated herein by reference; the citation of any document is not to be construed as an admission that it is prior art with respect to the present invention.

DETAILED DESCRIPTION OF THE INVENTION

I. Terms and Definitions:

The following is a list of definitions for terms used herein:

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

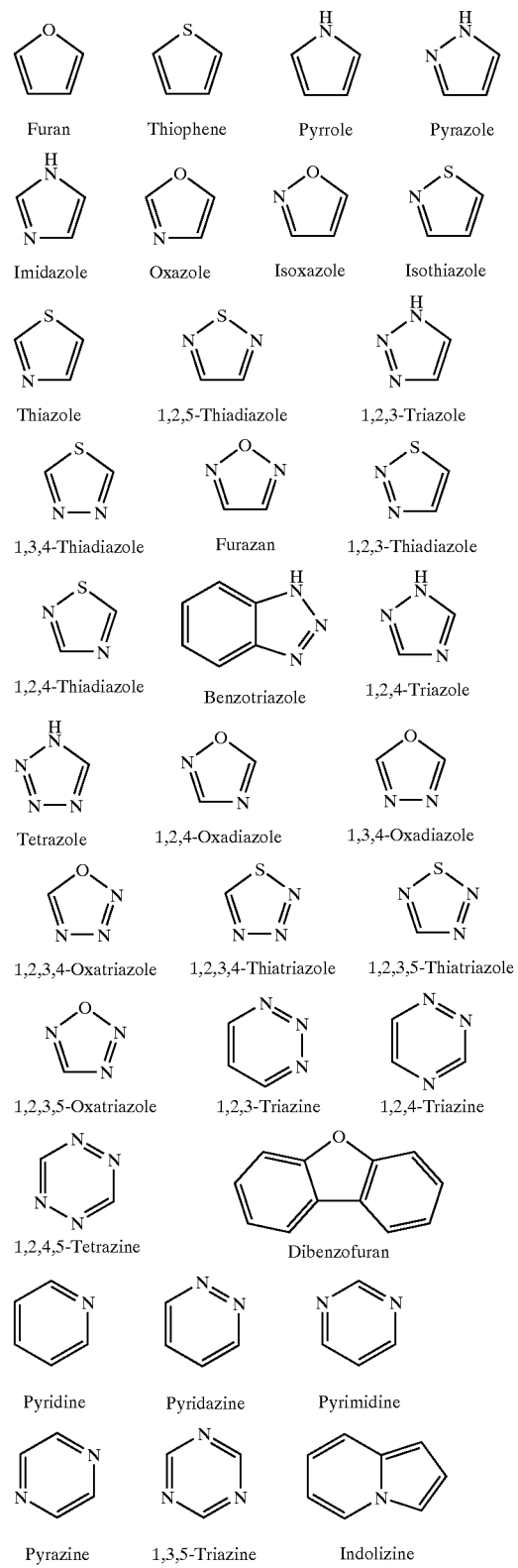

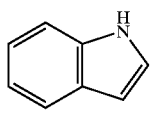 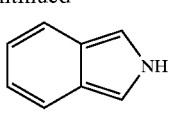

Indole      Isoindole

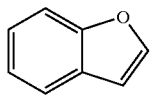 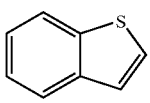

Benzofuran      Benzothiophene

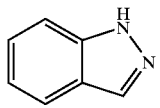 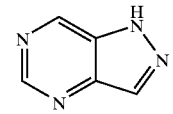

1H-Indazole      Purine

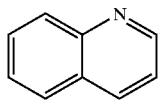 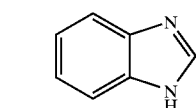

Quinoline      Benzimidazole

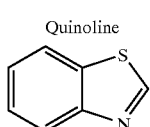 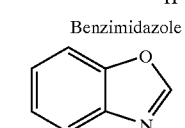

Benzthiazole      Benzoxazole

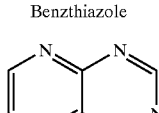 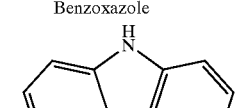

Pteridine      Carbazole

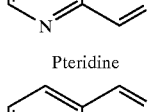 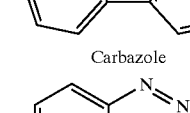

Isoquinoline      Cinnoline

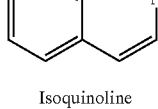 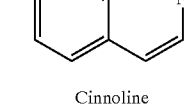

Phthalazine      Quinazoline

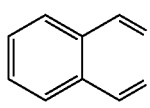 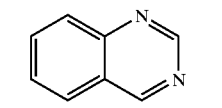

Quinoxaline      1,8-Napthypyridine

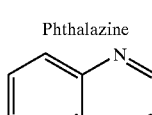 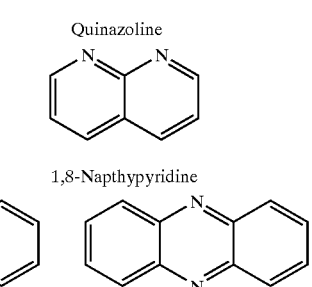

Acridine      Phenazine

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

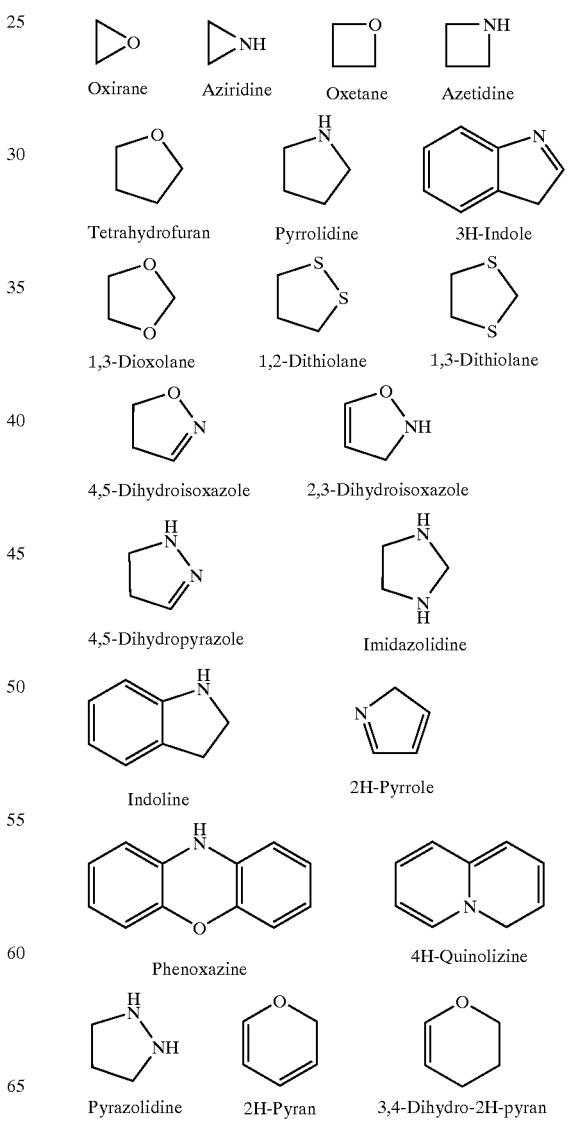

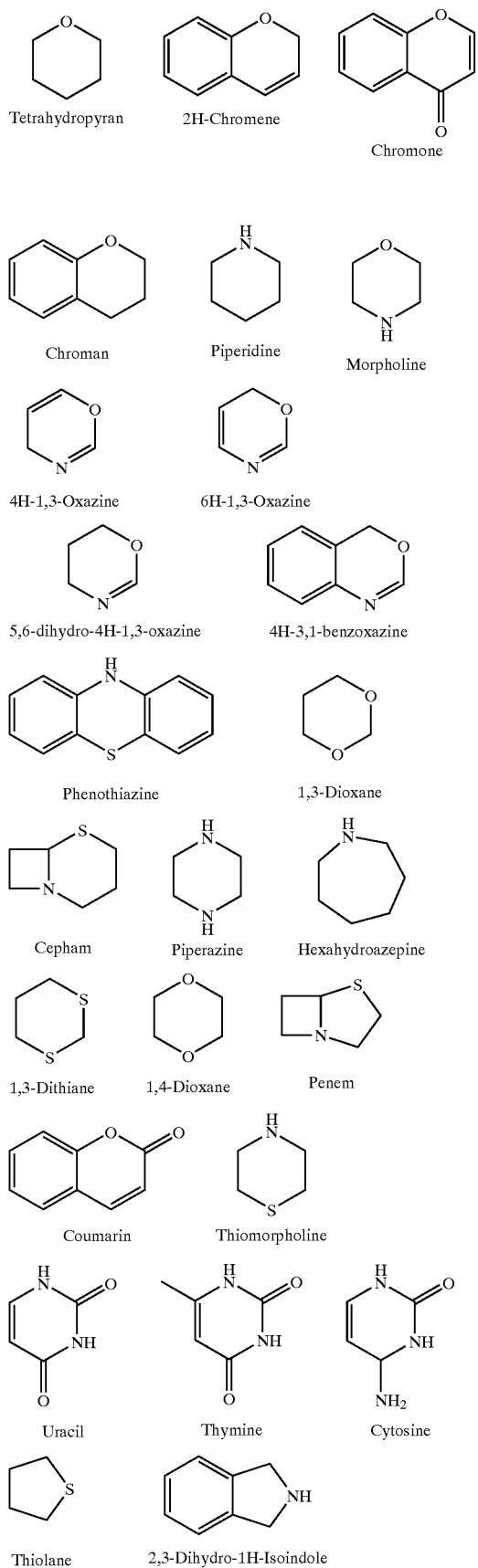

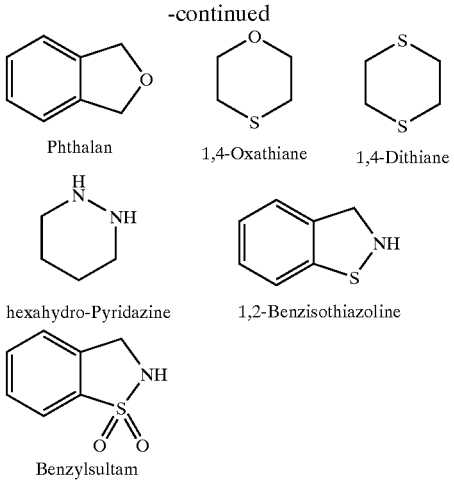

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two Nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published September 11. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide compound of the present invention that does not interfere with the activity of the compound, or that is readily converted in vivo by an animal, preferably a mammal, more preferably a human subject, to yield a pharmaceutically active compound. Examples of such amide derivatives are alkoxyamides, where the hydroxyl hydrogen of the hydroxamic acid of a Formula (I) compound is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing compound of the present invention that does not interfere with the activity of the compound, or that is readily converted in vivo by an animal, preferably a mammal, more preferably a human subject to yield a pharmaceutically active compound. Examples of such imide derivatives are those where the amino hydrogen of the hydroxamic acid of a Formula (I) compound is replaced by an acyl moiety (i.e., R—C(=O)—).

A "biohydrolyzable ester" is an ester of a carboxylic acid-containing compound of the present invention that does not interfere with the activity of the compound or that is readily converted by an animal to yield a pharmaceutically active compound. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a compound of formula (I)) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the inventive compound (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

II. Compounds

The subject invention involves compounds of Formula (I):

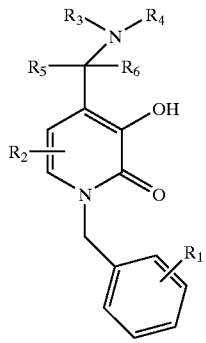

The following provides a description of particularly preferred moieties, but is not intended to limit the scope of the claims.

Each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, and heterocycloalkyl. In one embodiment, R is hydrogen.

Each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, and heterocycloalkyl. In one embodiment, $R^2$ is hydrogen.

$R^3$ and $R^4$ are each independently chosen from hydrogen, alkyl, alkenyl, alkynyl, heteroalkyl, aryl, heteroaryl, cycloalkyl, heterocycloalkyl, alkylheteroalkyl, alkylaryl, alkylheteroaryl, alkylcycloalkyl and alkylheterocycloalkyl; or $R^3$ and $R^4$, together with the Nitrogen atom to which they are bonded, join to form heteroaryl, or heterocycloalkyl moieties, optionally substituted with at least hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, heterocycloalkyl, spirocyloalkyl and combinations thereof.

$R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, and heterocycloalkyl. In one embodiment, $R^5$ and $R^6$ are each hydrogen.

III. Compound Preparation:

The compounds of the invention can be prepared using a variety of procedures. Particularly preferred syntheses are described in the following general reaction scheme. (The R groups used to illustrate the reaction schemes do not necessarily correlate to the respective R groups used to describe the various aspects of the Formula I compounds. That is, for example, $R^1$ in Formula (I) does not represent the same moiety as $R^1$ here). Specific examples for making the compounds of the present invention are set forth in Section VII, below.

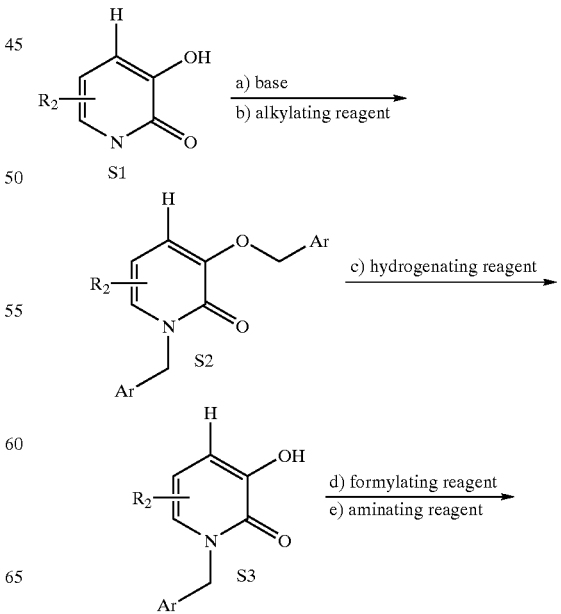

General Scheme

-continued

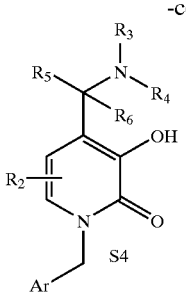

In general scheme I, the starting material S1 is known, made by known methods, or are commercially available. S1 is protected by being subjected to an alkylating agent in the presence of base in an alcohol solvent to produce compound S2, wherein "Ar" is defined as an aryl moiety. As used herein, "alkylating agent" means an agent that reacts with S1 resulting in both the nitrogen and hydroxyl of S1 forming a new carbon-nitrogen and carbon-oxygen bond, respectively. Non-limiting examples of an alkylating agent include halomethylenearyl or halomethyleneheteroaryl. An example of an alcohol solvent is methanol. Suitable examples of base include potassium hydroxide, potassium carbonate, potassium tert-butoxide, sodium methoxide, and Triton B.

In turn, S2 is selectively deprotected by a hydrogenating agent to yield S3. As used herein, "hydrogenating agent" means addition of hydrogen atom to another atom residue like carbon. Suitable example of a hydrogenating agent include palladium on carbon or rhodium on carbon, in a methanol solvent and under hydrogen gas.

Lastly, S3 is formylated and aminated by a formylating agent and an aminating agent, respectively. As used herein, "formylating agent" means an agent that transfers a methylene unit "$CH_2$" or

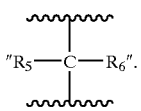

Non-limiting examples of a formylating agent are paraformaldehyde, formaldehyde, formic acid-formamide, formylimidazole, p-nitrophenyl formate. Alternatively, any aldehyde (R—COH) can be used as formylating agent in this application. The result is that the methylene unit is further branched based upon the aldehyde that is used. These formulating agents are commercially available or made by known methods. As used herein, "aminating agent" means any primary of amine of formula $NHR^3$ or secondary amine of formula $NR^3R^4$. These amines are commercially available or made by known methods. For example, many such amines can be identified using ChemOffice WebServer and the ChemACX databases. These amines can be further modified by those methods well-known in the art.

These steps may be varied to increase yield of desired product. The skilled artisan will recognize the judicious choice of reactants, solvents, and temperatures as an important components in any successful synthesis. Determination of optimal conditions, etc. is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Methods of Use:

The compounds of the present invention are useful as antimicrobials. Without wishing to be bound by theory, these compounds could act as chelators of the cobalt ion of the bMap active site. As chelators, these compounds could as act as inhibitors of metalloenzymes.

V. Compositions:

The compositions of the invention comprise:
 (a) a safe and effective amount of a compound of the invention; and
 (b) a pharmaceutically-acceptable carrier.

The invention compounds can therefore be formulated into pharmaceutical compositions for use in treatment microbial infections. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to destroy or suppress the growth or reproduction of microorganisms, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugarcoated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel™ RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VI. Methods of Administration

This invention also provides methods of treating a microbial infection in a human or other animal subject, by administering a safe and effective amount of a Formula (I) compound to said subject.

Compositions of this invention can be administered topically or systemically. Systemic application includes any method of introducing Formula (I) compound into the tissues of the body, e.g., transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site infection, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

For localized conditions, topical administration is preferred. For example, to treat an microbial infection of the eye, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of a microbial infection of the skin, the compound is applied locally and topically, in a gel, paste, salve or ointment. For treatment of oral infections, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

VII. Examples

Compound Preparation

The following substructure and table show the structure of Examples 1–38 compounds made according to the procedures described herein below. The R or X groups used to illustrate the compound examples do not necessarily correlate to the respective R and X groups used to describe the various moieties of Formula (I) in the claims.

A. Synthesis of Preferred Intermediate N-benzyl-3-hydroxypyridin-2-one

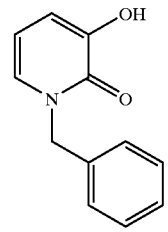

1-Benzyl-3-benzyloxy-1H-pyridin-2-one (Ghosh etal, *J. Org. Chem.* 1989, 54, 5073) is dissolved in anhydrous methanol (10 mL) and to the thoroughly degassed solution is added a catalytic amount of Pd—C (0.1%). The mixture is hydrogenated under a balloon of hydrogen, until all the starting material is consumed. At the completion, the solution is filtered through Celite™. The solvent is removed in vacuo, and the residue is washed with ether, to afford the desired product. $^1$H NMR (300 MHz, CDCl$_3$) δ 5.15 (s, 2H), 6.14 (t, J=7.2 Hz, 1H); 6.71 (m, 1H), 7.31 (6H) 9.07 (s, 1H).

B. General Procedure for the Three Component Coupling Between Pyridones, Formaldehyde and Amines: Pyridone intermediate of step A (1 eqv.), HCHO or aldehyde (2.2 eqv.) are mixed together in aqueous EtOH (10 mL) and stirred for 30 min. Amine (2.2 eqv.) is added, stirred for 12 h, and concentrated. The residue is dissolved in EtOH (10 mL) and purified via HPLC (water/acetonitrile/0.1% TFA). The product is isolated as the TFA salt unless indicated otherwise. The yields are 75–95%.
C. Examples 1–38
Examples are prepared in accordance with the above method by varying the amine.
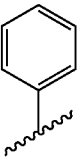
| Example | R1 | X |
|---|---|---|
| 1 | 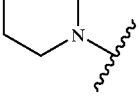 | 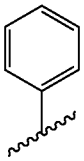 |
| 2 | 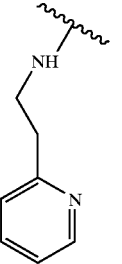 |  |
| 3 | 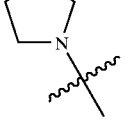 |  |
| 4 | 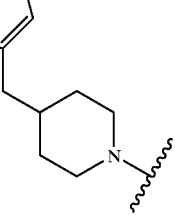 | 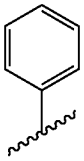 |
| 5 | 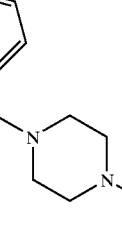 | 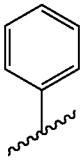 |
-continued
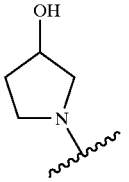
| Example | R1 | X |
|---|---|---|
| 6 | 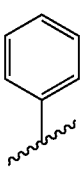 | 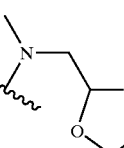 |
| 7 | 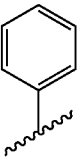 | 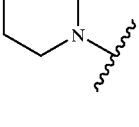 |
| 8 | 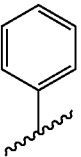 | 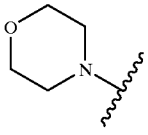 |
| 9 | 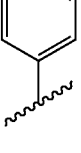 | 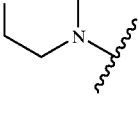 |
| 10 | 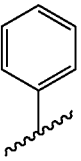 | 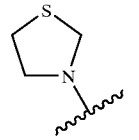 |
| 11 | 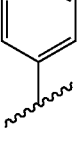 | 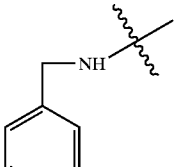 |

-continued
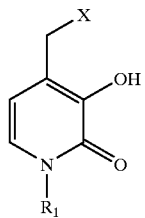
| Example | R1 | X |
|---|---|---|
| 12 | 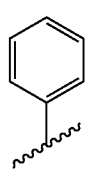 | 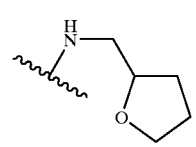 |
| 13 | 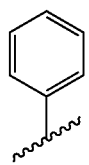 | 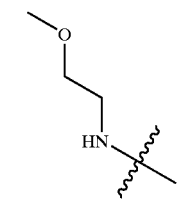 |
| 14 | 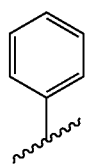 | 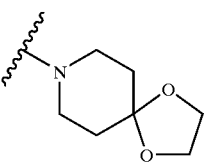 |
| 15 | 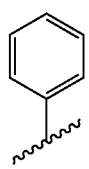 | 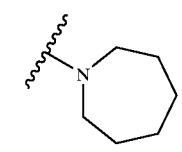 |
| 16 | 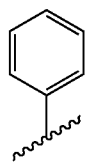 | 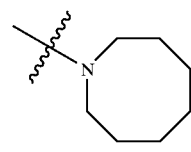 |
| 17 | 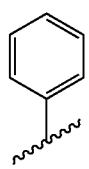 | 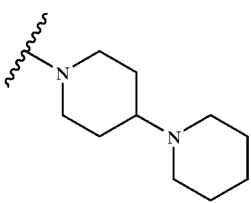 |
| 18 | 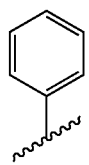 | 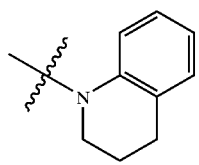 |
-continued
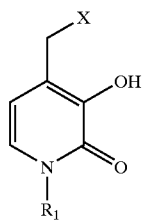
| Example | R1 | X |
|---|---|---|
| 19 |  | 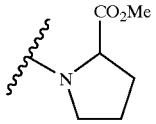 |
| 20 |  | 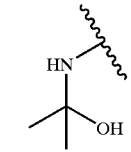 |
| 21 | 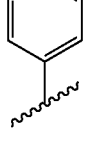 | 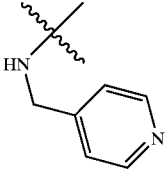 |
| 22 |  | 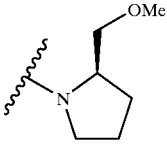 |
| 23 | 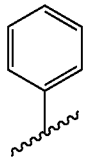 | 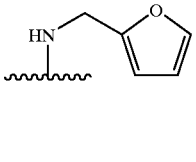 |
| 24 | 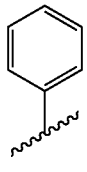 | 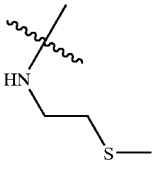 |
| 25 | 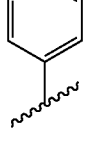 | 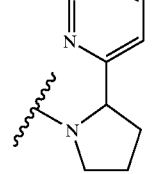 |

-continued

![structure](pyridinone with X-CH2 at 4-position, OH at 3-position, =O at 2-position, R1 on N)

| Example | R1 | X |
|---|---|---|
| 26 | phenyl | HN-CH2-C6H4-4-OMe |
| 27 | phenyl | HN-CH(CH3)-C6H4-4-OMe |
| 28 | phenyl | piperazinyl-(6-chloropyridazin-3-yl) |
| 29 | phenyl | HN-CH2CH2-imidazol-1-yl |
| 30 | phenyl | HN-cycloheptyl |
| 31 | phenyl | HN-(4-methylcyclohexyl) |
| 32 | phenyl | HN-(1-benzylpiperidin-4-yl) |

-continued

![structure](pyridinone with X-CH2 at 4-position, OH at 3-position, =O at 2-position, R1 on N)

| Example | R1 | X |
|---|---|---|
| 33 | phenyl | HN-(azepan-2-one-3-yl) |
| 34 | phenyl | HN-(1-benzylpyrrolidin-3-yl) |
| 35 | 2-methoxyphenyl | pyrrolidin-1-yl |
| 36 | pyridin-4-yl | pyrrolidin-1-yl |
| 37 | phenyl | 4-(2-methoxyphenyl)piperazin-1-yl |
| 38 | phenyl | HN-C(CH3)=CH-C6H5 (or HN-CH(CH3)-Ph style) |

Example 1

1-Benzyl-3-Hydroxy-4-piperidin-1-ylmethyl-1H-pyridin-2-one $^1$H NMR (300 MHz, CD$_3$OD) δ 1.81 (m, 6H), 3.07 (m, 2H), 3.51 (m, 2H), 4.23 (s, 2H), 5.24 (s, 2H), 6.31 (d, J=6.9 Hz, 1H), 7.35 (m, 6H); $^{19}$F NMR (252 MHz, CD$_3$OD) δ 85.5; 13C NMR (75 MHz, DMSO) δ 21.3, 22.7, 51.8, 52.5, 53.1 106.4, 117.4, 127.7, 128.0, 128.2, 128.9, 137.3, 147.4, 158.0; ES MS(M+1) 299.12; HRMS Calcd. For C$_{18}$H$_{22}$N$_2$O$_2$, 298.38. Found (M+1) 299.17.

Example 2

1-Benzyl-3-Hydroxy-4-morpholin-1-ylmethyl-1H-pyridin-2-one $^1$H NMR (300 MHz, DMSO) δ 3.25 (m, 4H), 3.81 (m, 4H), 4.18 (s, 2H), 5.17 (s, 2H), 6.31 (d, J=6.9 Hz, 1H), 7.35 (m, 6H); $^{19}$FNMR (300 MHz, DMSO) δ 88.5; $^{13}$C NMR (300 MHz, DMSO) δ 51.6, 51.8, 53.4, 63.5, 107.9, 119.1, 127.8, 128.0, 128.2, 128.9, 137.3, 147.5, 158.3; ES MS(M+1) 301.12; HRMS Calcd. For $C_{17}H_{20}N_2O_3$, 300.35.

Example 3

-Benzyl-3-Hydroxy-4-thiamorpholin-1-ylmethyl-1H-pyridin-2-one $^1$HNMR(300 MHz, DMSO) δ 2.92 (m, 4H), 3.38 (m, 4H), 4.17 (s, 2H), 5.16 (s, 2H), 6.29 (d, J=7.5 Hz, 1H), 7.34 (m, 6H), 9.97 (s, 1H); $^{19}$F NMR (300 MHz, DMSO) δ 88.4; $^{13}$C NMR (75 MHz, DMSO) δ 24.3, 51.9, 53.4, 53.7, 107.9, 110.9, 127.8, 128.0, 128.2, 128.8, 137.2, 147.6, 157.6; ES MS (M+1) 317.14; HRMS Calcd. For $C_{17}H_{20}N_2O_2S$, 316.42. Found: (M+1) 317.13.

Example 4

1-Benzyl-3-Hydroxy-4-thiazolidin-1ylmethyl-1H-pyridin-2-one $^1$HNMR (300 MHz, DMSO) δ 3.09 (t, J=6.3 Hz, 2H), 3.42 (t, J=6.3 Hz, 2H), 4.03 (s, 2H), 4.29 (s, 2H), 5.16 (s, 2H), 6.34 (d, J=7.2 Hz, 1H), 7.34 (m, 6H), 10.48 (broad s, 1H); $^{19}$FNMR (300 MHz, DMSO) δ 87.9; $^{13}$CNMR (75 MHz, DMSO) δ 28.3, 48.3, 50.1, 56.3, 57.0, 107.4, 122.1, 127.8, 128.2, 128.8, 137.4, 146.3, 157.6; ES MS (M+1) 303.08; Anal. Calcd for $C_{18}H_{19}N_2O_4SF$, C, 51.92; H, 4.60; N, 6.73; S, 7.70. Found: C, 51.67; H, 4.48; N, 6.69; S, 7.65.

Example 5

1-Benzyl-4-(benzylaminomethyl)-3-hydroxy-1H-pyridin-2-one $^1$HNMR (300 MHz, DMSO) δ 4.01 (s, 2H), 4.20 (s, 2H), 5.16 (s, 2H), 6.34 (d, J=7.2 Hz, 1H), 7.36 (m, 11H), 9.16 (broad s, 1H); $^{19}$FNMR(252 MHz, DMSO) δ 88.6; $^{13}$C NMR (75 MHz, DMSO) δ; ES MS(M+1) 321.16; Anal. Calcd. For $C_{22}H_{21}F_3N_2O_4$, C, 60.83; H, 4.87; N, 6.45. Found: C, 60.75; H, 4.56; N, 6.34.

Example 6

1-Benzyl-3-Hydroxy-4-[(2-pyridin-2-ylethylamino)methyl]-1H-pyridin-2-one $^1$H NMR (300 MHz, DMSO) δ 3.26 (m, 2H), 3.37 (m, 2H), 4.08 (s, 2H), 5.17 (s, 2H); 6.34 (d, J=7:2 Hz, 1H), 7.38 (m, 6H), 7.86 (d, J=5.7 Hz, 2H), 8.84 (m, 2H), 9.32 (broad s, 1H); $^{19}$FNMR(252 MHz, DMSO) δ 88.6; $^{13}$C NMR (75 MHz, DMSO) δ 31.5, 44.1, 46.3, 51.8, 106.9, 114.8, 127.1, 128.1, 128.8, 137.4, 143.8, 146.1, 155.3, 157.5, 158.4; ES MS (M+1) 336.18; HRMS Calcd For $C_{20}H_{21}N_3O_2$, 335.40. Found: 336.16.

Example 7

1-Benzyl-3-Hydroxy-4-pyrrolidin-1-ylmethyl-1H-pyridin-2-one $^1$H NMR (300 MHz, DMSO) δ 1.96 (s, 4H), 3.16 (s, 2H), 3.43 (s, 4H), 4.23 (s, 4H), 5.17 (s, 2H), 6.34 (d, J=7.2 Hz, 1H), 7.34 (m, 6H); $^{19}$F NMR (252 MHz, DMSO) δ 88.7; $^{13}$C NMR (75 MHz, DMSO) δ 22.8, 50.9, 51.8, 53.7, 107.3, 118.0, 128.0, 128.2, 128.9, 137.3, 146.7, 157.6; ES MS (M+1) 285.13; Anal. Calcd. For $C_{19}H_{21}F_3N_2O_4$, C, 57.28; H, 5.31; N, 7.03. Found: C, 57.10; H, 5.11, N, 7.02.

Example 8

1-Benzyl-4-(4-benzylpiperdin-1-ylmethyl)-3-hydroxy-1H-pyridin-2-one $^1$H NMR (DMSO) δ 1.43 (m, 2H), 1.72 (m, 4H), 2.96 (m, 2H), 3.41 (m, 3H), 4.09 (s, 2H), 5.16 (s, 2H), 6.34 (d, J=7.2 Hz, 1H), 7.35 (m, 11H); $^{19}$F NMR (252 MHz, DMSO) 88.8; $^{13}$C NMR (75 MHz, DMSO) δ; ES MS(M+1) 389.21; HRMS Calcd. For $C_{25}H_{28}N_2O_2$, 388.50. Found (M+1) 389.22.

Example 9

1-Benzyl-4-(4-benzylpiperazine-1-ylmethyl)-3-hydroxy-1H-pyrdin-2-one $^1$H NMR (300 MHz, DMSO) δ 3.11 (broad s, 4H), 3.81 (s, 2H), 4.18 (s, 2H), 5.15 (s, 2H), 6.24 (d, J=7.2 Hz, 1H), 7.34 (m, 6H), 7.46 (m, 5H); $^{19}$F NMR (252 MHz, DMSO) δ 88.2; 13C (75 MHz, DMSO) δ; ES MS(M+1) 390.21; HRMS Calcd. For $C_{24}H_{27}N_3O_2$, 389.49. Found (M+1) 390.21.

Example 10

1-Benzyl-3-Hydroxy-4-(3-hydroxypyrrolidin-1-ylmethyl)-1H-pyrdin-2-one $^1$HNMR (300 MHz, DMSO) δ 1.90 (m, 1H), 3.18 (m, 2H), 3.47 (m, 3H), 4.24 (s, 2H), 4.43 (s, 1H), 5.17 (s, 2H), 6.34 (d, J=7.2 Hz, 1H), 7.34 (m, 6H); $^{19}$F NMR (252 MHz, DMSO) δ 89.0; $^{13}$C NMR (75 MHz, DMSO) δ 51.8, 52.6, 61.3, 68.6, 107.4, 117.9, 128.0, 128.2, 128.9, 137.3, 146.7, 157.6; ES MS(M+1) 301.13; HRMS Calcd. For $C_{17}H_{20}N_2O_3$, 300.35. Found: (M+1) 301.15.

Example 11

1-Benzyl-4-[([1,3]-dioxolan-2-ylmethylmethylamino)methyl]-3-hydroxy-1H-pyridin-2-one $^1$H NMR (300 MHz, DMSO) δ 2.81 (s, 3H), 3.35 (d, J=3.9 Hz, 2H), 3.89 (m, 2H), 4.01 (m, 2H), 4.21 (m, 2H), 5.17 (s, 2H); 5.27 (t, J=3.9 Hz, 1H), 6.34 (d, J=7.2 Hz, 1H), 7.35 (m, 6H); $^{19}$F NMR (252 MHz, DMSO) δ 88.5; $^{13}$C NMR (75 MHz, DMSO) δ; ES MS(M+1) 331.18; HRMS Calcd. For $C_{18}H_{22}N_2O_4$, 330.38. Found (M+1) 331.16.

Example 12

1-Benzyl-3-hydroxy-4-{[(tetrahydrofuran-2-ylmethyl)amino]methyl}-1H-pyrdin-2-one $^1$H NMR (300 MHz, DMSO) δ 1.56 (m, 1H), 1.86 (m, 2H), 1.99 (m, 1H), 2.92 (m, 1H), 3.05 (m, 1H), 3.80 (m, 2H), 4.09 (m, 3H), 5.16 (s, 2H), 6.34 (d, J=7.2 Hz, 1H), 7.34 (m, 6H); 8.91 (broad s, 1H); $^{19}$F NMR (252 MHz, DMSO) δ 88.5; $^{13}$C NMR(75 MHz, DMSO) δ; ES MS(M+1) 315.16; HRMS. Calcd. For $C_{18}H_{22}N_2O_3$, 314.38. Found (M+1) 315.16.

Example 13

1-Benzyl-3-hydroxy-4-[(2-methoxyethylamino)methyl]-1H-pyridin-2-one $^1$H NMR (300 MHz, DMSO) δ 3.13 (broad s, 2H), 3.30 (s, 3H), 3.59 (t, J=5.4 Hz, 2H), 4.02 (s, 2H), 5.16 (s, 2H), 6.34 (d, J=7.2 Hz, 1H), 7.34 (m, 6H), 8.91 (broad s, 1H); $^{19}$F NMR (252 MHz, DMSO) δ 88.4; $^{13}$C NMR (252 MHz, DMSO) δ; ES MS(M+1) 289.13; HRMS Calcd. For $C_{16}H_{20}N_2O_3$, 288.34. Found (M+1) 289.15.

Example 14

1-Benzyl-4-(1,4-dioxa-8-azaspiro[4,5]dec-8-ylmethyl)-3-hydroxy-1H-pyridin-2-one $^1$H NMR (300 MHz, DMSO) δ 1.90 (m, 4H), 3.11 (m, 2H), 3.43 (m, 2H), 3.93 (s, 4H), 4.19 (s, 2H), 5.16 (s, 2H), 6.34 (d, J=7.2 Hz, 1H), 7.34 (m, 6H), 10.01 (broad s, 1H) $^{19}$F NMR (252 MHz, DMSO) δ 88.3; $^{13}$C NMR (75 MHz, DMSO) δ 31.7, 50.7, 51.9, 52.5, 64.5, 101.1, 108.0, 116.5, 127.8, 128.0, 128.3, 128.9, 137.3, 147.5 157.6; ES MS(M+1) 357.19; HRMS Calcd. For $C_{20}H_{24}N_4O_2$, 356.42. Found (M+1) 357.18.

Example 15

4-Azepan-1-ylmethyl-1-benzyl-3-hydroxy-1H-pyridin-2-one $^1$H NMR (300 MHz, DMSO) δ 1.61 (m, 4H), 1.80 (m, 4H), 3.20 (m, 4H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ 22.8, 26.4, 51.8, 53.4, 54.4, 107.6, 117.2, 127.9, 128.0, 18.2, 128.9, 137.3, 147.2, 157.6; ES MS(M+1) 313.18; HRMS Calcd. For $C_{19}H_{24}N_2O_4$, 312.41. Found (M+1) 313.19.

Example 16

4-Azocan-1-ylmethyl-1-benzyl-3-hydroxy-1H-pyrdin-2-one $^1$H NMR (300 MHz, DMSO) δ 1.59 (m, 10H), 3.18 (m, 2H), 3.38 (m, 2H), 4.17 (s, 2H), 5.16 (s, 2H), 6.34 (d, J=7.2 Hz, 1H), 7.34 (m, 6H); $^{19}$F NMR (252 MHz, DMSO) δ 88.9; $^{13}$C NMR (75 MHz, DMSO) δ; ES MS(M+1) 327.2; HRMS Calcd. For $C_{20}H_{26}N_2O_2$, 326.43. Found (M+1) 327.20.

Example 17

1-Benzyl-4-{1,4'}-bipiperidinyl-1'-ylmethyl-3-hydroxy-1H-pyridin-2-one $^1$H NMR (300 MHz, DMSO) δ 1.43–1.98 (m, 10H), 2.21 (m, 2H), 3.01 (m, 4H), 3.43 (m, 3H), 4.12 (s, 2H), 5.16 (s, 2H), 6.34 (d, J=7.2 Hz, 1H), 7.34 (m, 6H), 9.85 (broad s, 1H); $^{19}$F NMR (252 MHz, DMSO) δ 88.7; $^{13}$C NMR (75 MHz, DMSO) δ 21.6, 22.9, 23.8, 49.6, 50.5, 51.8, 53.0, 59.5, 108.0, 127.8, 128.0, 128.2, 128.9, 137.3, 147.5, 157.6; ES MS(M+1) 382.4; HRMS Calcd. For $C_{23}H_{31}N_3O_2$, 383.51. Found (M+1) 382.25.

Example 18

1-Benzyl-4-(3,4-dihydro-2H-quinolin-1-ylmethyl)-3-hydroxy-1H-pyridin-2-one $^1$H NMR (300 MHz, DMSO) δ 3.13 (t, J=6.3 Hz, 2H), 3.52 (m, 2H), 4.28 (s, 2H), 4.41 (s, 2H), 5.18 (s, 2H), 6.34 (d, J=7.2 Hz, 1H), 7.23–7.41 (m, 10H), 10.15 (broad s, 1H); $^{19}$FNMR (252 MHz, DMSO) δ 88.9; $^{13}$C NMR (75 MHz, DMSO) δ 25.4; 49.3, 51.8, 52.7, 52.9, 107.6, 11.6, 116.8, 126.9, 127.0, 127.9, 128.0, 128.1, 128.2, 128.9, 131.7, 137.3, 147.3, 157.6; ES MS(M+1) 347.40; HRMS Calcd. For $C_{22}H_{22}N_2O_2$, 346.42. Found (M+1) 347.17.

Example 19

1-(1-Benzyl-3-hydroxy-2-oxo-1,2-dihydropyridin-4-ylmethyl)pyrrolidine-2-carboxylic acid methyl ester $^1$H NMR (300 MHz,.DMSO) δ 2.01 (m, 3H), 2.45 (m, 1H), 3.26 (m, 1H), 3.53 (m, 1H), 3.69 (s, 3H), 4.30 (m, 3H), 5.17 (s, 2H), 6.27 (d, 6.9 Hz, 1H), 7.35 (m, 6H), $^{19}$F NMR (252 MHz, DMSO) δ 88.3; 13C NMR (75 MHz, DMSO) δ; ES MS(M+1) 343.20; HRMS Calcd. For $C_{19}H_{22}N_2O_4$, 342.39. Found (M+1)

Example 20

1-Benzyl-3-hydroxy-4-[(2-hydroxy-1,1-dimethylethylamino)methyl]-1H-pyridin-2-one $^1$H NMR (300 MHz, DMSO) d 1.27 (s, 6H), 3.49 (s, 2H), 3.95 (s, 2H), 5.17 (s, 2H) 6.34 (d, J=7.2 Hz, 1H), 7.34 (m, 6H), 8.47 (broad s, 2H), 9.94 (broad s, 1H); $^{19}$F NMR (252 MHz, DMSO) δ 88.7; 13C NMR (75 MHz, DMSO) δ; ES MS(M+1) 303.19; HRMS Calcd. For $C_{17}H_{22}N_2O_3$, 302.37. Found (M+1) 303.17.

Example 21

1-Benzyl-3-hydroxy-4-{[(pyridin-4-ylmethyl)amino]methyl}-1H-pyridin-2-one $^1$H NMR (300 MHz, DMSO) δ 4.07 (s, 2H), 4.32 (s, 2H), 5,16 (s, 2H), 6.34 (d, J=7.2 Hz, 1H), 7.34 (m, 6H); 7.62 (d, J=5.7 Hz, 2H), 8.71 (d, J=4.5 Hz, 2H); $^{19}$F NMR (252 MHz, DMSO) δ 88.0; $^{13}$C NMR (75 MHz, DMSO) δ; ES MS(M+1) 322.17; HRMS Calcd. For $C_{19}H_{19}N_3O_2$, 321.37. Found (M+1) 322.15.

Example 22

1-Benzyl-3-hydroxy-4-(2-methoxymethylpyrrolidin-1-ylmethyl)-1H-Pyrdin-2-one

1H NMR (300 MHz, DMSO) δ 1.71 (m, 1H), 1.84 (m, 1H), 1.99 (m, 1H), 2.15 (m, 1H), 3.19 (m, 1H), 3.30 (s, 3H), 3.41 (m, 1H), 3.62 (m, 2H), 3.77 (m, 1H), 4.15 (m, 1H), 4.39 (m, 1H), 5.17 (s, 2H), 6.34 (d, J=7.2 Hz, 1H), 7.34 (m, 6H); 9.60 (broad s, 1H); $^{19}$F NMR (252 MHz, DMSO) δ 88.3; $^{13}$C NMR (75 MHz, DMSO) δ; ES MS(M+1) 329.2; HRMS Calcd. For $C_{19}H_{24}N_2O_3$, 328.41. Found (M+1)

Example 23

1-Benzyl-4-{[(furan-2-ylmethyl)amino]methyl}-3-hydroxy-1H-pyrdin-2-one $^1$H NMR (300 MHz, DMSO) δ 4.00 (s, 2H), 4.28 (s, 2H), 5.16 (s, 2H), 6.27 (d, J=6.9 Hz, 1H), 6.54 (m, 1H), 6.65 (m, 1H), 7.34 (m, 6H), 7.80 (m, 1H), 9.27 (broad s, 1H); $^{19}$F NMR (252 MHz, DMSO) δ 88.3; $^{13}$C NMR (75 MHz, DMSO) δ; ES MS(M+1) 323.15; HRMS Calcd. For $C_{18}H_{18}N_2O_3$, 310.35. Found (M+1)

Example 24

1-Benzyl-3-hydroxy-4-[(2-methylsulfanylethylamino)methyl]-1H-pyridin-2-one $^1$H NMR (300 MHz, DMSO) δ 2.10 (s, 3H), 2.74 (t, J=6.9 Hz, 2H), 3.16 (t, J=8.1 Hz, 2H), 4.05 (s, 2H), 5.17 (s, 2H), 6.34 (d, J=7.2 Hz, 1H), 7.34 (m, 6H), 19F NMR (252 MHz, DMSO) δ 89.0; ES MS(M+1) 305.14, HRMS Calcd. For $C_{16}H_{20}N_2O_2S$, 304.41. Found (M+1)

Example 25

1-Benzyl-3-hydroxy-4-(2-pyrdin-2-ylpyrrolidin-1-ylmethyl)-1H-pyridin-2-one $^1$H NMR (300 MHz, DMSO) δ 2.12 (m, 4H), 3.39 (m, 1H), 3.63 (m, 1H), 4.07 (m, 2H), 4.60 (m, 1H), 5.10 (m, 2H), 6.15 (d, J=6.9 Hz, 1H), 7.33 (m, 6H), 7.44 (m, 1H), 8.05 (d, J=8.1 Hz, 1H), 8.59 (d, J=4.8 Hz, 1H), 8.74 (s, 1H); $^{19}$F NMR (252 MHz, DMSO) δ 88.0; ES MS(M+1) 362.22; HRMS Calcd. For $C_{22}H_{23}N_3O_2$, 361.44. Found (M+1)

Example 26

1-Benzyl-3-hydroxy-4-[(4-methoxybenzylamino)methyl]-1H-pyridin-2-one $^1$H NMR (300 Mhz, DMSO) δ 3.70 (s, 3H), 3.98 (s, 2H), 4.13 (s, 2H), 5.16 (s, 2H), 6.28 (d, J=7.5 Hz, 1H), 7.00 (d, J=9.0 Hz, 4H), 7.34 (m, 6H); 9.07 (broad s, 1H); $^{19}$F NMR (252 MHz, DMSO) δ 89.0; ES MS(M+1) 351.10; HRMS Calcd. For $C_{21}H_{22}N_2O_3$, 350.41. Found (M+1) 351.17.

Example 27

4-((1-(4-methoxyphenyl)ethylamino)methyl-I-benzyl-3-hydroxypyridin-2(1H)-one $^1$H NMR (300 MHz, DMSO) δ 1.59 (d, J=7.2 Hz, 3H), 3.71–3.93 (m, 2H), 4.45 (m, 1H), 5.15 (s, 2H), 6.28 (d, J=7.5 Hz, 1H), 7.34 (m, 11H); $^{19}$F NMR (252 MHz, DMSO) δ 88.9; $^{13}$C NMR (75 MHz, DMSO) δ 19.6, 42.5, 51.7, 58.0, 106.8, 119.3, 128.0, 128.1, 128.2, 128.9, 129.3, 129.4, 137.3, 145.9, 158.3; ES MS(M+1) 335.13; HRMS Calcd. For $C_{21}H_{22}N_2O_2$, 334.41. Found (M+1) 335.17.

Example 28

1-Benzyl-4-[4-(6-chloropyridazin-3-yl)piperazin-1-ylmethyl]-3-hydroxy-1H-pyridin-2-one $^1$H NMR (300 MHz, DMSO) δ 3.18 (m, 2H), 3.48 (m, 4H), 4.19 (s, 2H), 4.46 (m, 2H), 5.16 (s, 2H), 6.62 (d, J=7.2 Hz, 1H), 7.35 (m, 6H), 7.48 (m, 1H), 7.68 (m, 1H), 11.5 (broad s, 1H); $^{13}$C NMR (75 MHz, DMSO) δ 42.1, 50.3, 51.9, 52.5, 108.2, 116.2; 118.0, 128.0, 128.2, 128.9, 129.8, 137.3, 147.4, 157.6, 158.8; ES MS(M+1) 476.09. HRMS Calcd. For $C_{21}H_{22}ClN_5N_3O_2$, 411.88. Found (M+1) 412.76.

Example 29

1-Benzyl-3-hydroxy-4-[(3-imidazol-1-ylpropylamino)methyl]-1H-pyridin-2-one $^1$H NMR (300 MHz, DMSO) δ 2.19 (m, 2H), 2.97 (m, 2H), 4.02 (s, 2H), 4.30 (t, J=6.6 Hz, 2H); 5.17 (s, 2H), 6.30 (d, J=6.9 Hz, 1H), 7.36 (m, 6H), 7.26 (s, 1H), 7.76 (s, 1H), 9.03 (s, 1H), 9.11 (s, 1H); $^{19}$F NMR (252 MHz, DMSO) δ 88.5; 13C NMR (75 MHz, DMSO) δ 26.5, 44.0, 46.0, 51.8, 106.8, 118.7, 120.5, 122.2, 127.9, 128.2, 128.9, 135.8, 137.4, 146.0, 158.2; ES MS(M+1) 339.05; HRMS Calcd. For $C_{19}H_{22}N_4O_2$, 338.44. Found (M+1) 339.18.

Example 30

1-Benzyl-4-cycloheptylaminomethyl-3-hydroxy-1H-pyrdin-2-one $^1$H NMR (300 MHz, DMSO) δ 1.55 (m, 10H), 2.03 (m, 2H), 3.18 (s, 1H), 3.99 (m, 2H), 5.17 (s, 2H), 6.32 (d, J=6.9 Hz, 1H), 7.35 (m, 6H), 8.65 (broad s, 2H), 9.98 (broad s, 1H); $^{19}$F NMR (252 MHz, DMSO) d 88.6; $^{13}$C NMR (75 MHz, DMSO) δ 23.0, 27.2, 30.4, 41.6, 51.7, 58.9, 107.0, 111.7, 127.9, 128.0, 128.2, 128.8, 137.4, 146.0, 157.5; ES MS(M+1) 327.13; HRMS Calcd. For $C_{20}H_{26}N_2O_2$, 326.43. Found (M+1) 327.20.

Example 31

1-Benzyl-3-hydroxy-4-[(4-methylcyclohexylamino)methyl]-1H-pyridin-2-one $^1$H NMR (300 MHz, DMSO) δ 0.93 (d, J=6.9 Hz, 3H), 1.38 (m, 4H), 1.74 (m, 4H), 2.05 (m, 1H), 3.10 (m, 1H), 4.01 (s, 2H), 5.17 (s, 2H), 6.31 (m, 1H), 7.34 (m, 6H), 8.05 (broad s, 2H), 9.98 (broad s, 1H); $^{19}$F NMR (252 MHz, DMSO) δ 88.9; $^{13}$C NMR (75 MHz, DMSO) δ; ES MS(M+1) 327.14; HRMS Calcd. For $C_{20}H_{26}N_2O_2$, 326.43; Found (M+1) 372.20.

Example 32

1-Benzyl-4-[(1-benzylpiperidin-4-ylamino)methyl]-3-hydroxy-1H-pyridin-2-one $^1$H NMR (300 MHz, DMSO) δ 1.77 (m, 2H), 2.31 (m, 2H), 2.98 (m, 2H), 3.30 (m, 3H), 3.46 (m, 2H), 4.03 (s, 2H), 0.29 (s, 2H), 5.16 (s, 2H), 6.30 (d, J=7.5 Hz, 1H), 7.34 (m, 6H), 7.49 (s, 5H), 9.12 (broad s, 1H), 10.05 (broad s, 1H); $^{19}$F NMR (252 MHz, DMSO) δ 88.8; $^{13}$C NMR (75 MHz, DMSO) δ 27.1, 43.4, 51.8, 52.1, 54.2, 54.7, 57.6, 106.9, 118.5, 128.0, 128.1, 128.8, 129.3, 129.8, 130.7, 131.3, 137.3, 146.2, 157.4; ES MS(M+1) 404.56; HRMS Calcd. For $C_{25}H_{28}N_3O_2$, 403.52. Found (M+1) 404.23.

Example 33

3-[(1-Benzyl-3-hydroxy-2-oxo-1,2-dihydropyridin-4-ylmethylamino]azepan-2-one $^1$H NMR (300 MHz, DMSO) δ 1.25 (m, 1H), 1.59 (m, 2H), 1.74 (m, 1H), 1.92 (m, 1H), 2.10 (m, 1H), 3.18 (m, 3H), 4.03 (s, 2H), 4.2 (m, 1H), 5.17 (s, 2H), 6.33 (d, J=7.5 Hz, 1H), 7.34 (m, 6H), 8.31 (t, J=5.4 Hz, 1H), 9.07 (broad s, 2H), 9.90 (broad s, 1H); $^{19}$F NMR (252 MHz, DMSO) δ 88.4; $^{13}$C NMR (75 MHz, DMSO) δ 27.0, 27.2, 28.4, 43.4, 51.7, 59.3, 107.1, 118.9, 127.8, 127.9, 128.1, 128.9, 137.4, 146.0, 157.5, 166.3; ES MS(M+1) 342.01; HRMS Calcd. For $C_{19}H_{23}N_3O_3$, 341.40. Found (M+1) 342.18.

Example 34

1-Benzyl-4-[(1-benzylpyrrolidin-3-ylamino)methyl]-3-hydroxy-1H-pyridin-2-one $^1$H NMR (300 MHz, DMSO) δ 2.22 (m, 2H), 2.42 (m, 1H), 3.39 (m, 3H), 3.68 (m, 1H), 4.06 (s, 2H), 4.39 (s, 2H), 5.17 (s, 2H), 6.33 (d, J=7.5 Hz, 1H), 7.30–7.52 (m, 11H); $^{19}$F NMR (252 MHz, DMSO) δ 88.5; 13C NMR (75 MHz, DMSO) δ 27.1, 43.4, 51.8, 52.1, 54.2, 54.7, 57.5, 106.9, 118.5, 128.0, 128.1, 128.8, 129.3, 129.8, 130.7, 131.3, 137.3, 146.2, 157.5; ES MS(M+1) 390.14; HRMS Calcd. For $C_{24}H_{27}N_3O_2$, 389.49. Found (M+1) 390.21.

Example 35

3-Hydroxy-1-(3-methoxybenzyl)-4-pyrrolidin-1-ylmethyl-1H-pyridin-2-one $^1$H NMR (300 MHz, DMSO) δ 1.89 (m, 2H), 1.99 (m, 2H), 3.07 (m, 2H), 3.41 (m, 2H), 3.74 (s, 3H), 4.17 (m, 2H), 5.17 (s, 2H), 6.51 (d, J=7.2 Hz, 1H), 6.90 (m, 3H), 7.27 (t, J=7.5 Hz, 1H), 7.37 (d, J=7.2 Hz, 1H), 9.98 (broad s, 1H), 10.72 (broad s, 1H); $^{13}$C NMR (75 MHz, DMSO) δ 23.0; 50.3, 51.7; 53.2; 55.4, 107.6, 113.2, 114.2, 118.2, 120.3, 127.8, 130.0, 18.8, 146.4, 157.6, 159.6; ES MS(M+1) 315.82; HRMS Calcd. For $C_{18}H_{22}N_2O_3$, 314.38. Found (M+1) 315.17.

Example 36

3-Hydroxy-1-pyridin-4-ylmethyl-4-pyrrolidin-1-ylmethyl-1H-pyridin-2-one $^1$H NMR (300 MHz, DMSO) δ 1.81 (m, 4H), 3.05 (t, J=6.0 Hz, 4H), 4.23 (s, 2H), 5.48 (s, 2H), 6.76 (d, J=7.2 Hz, 1H), 7.49 (d, J=6.6 Hz, 1H), 7.83 (d, J=6.0 Hz, 2H), 8.89 (d, J=6.0 Hz, 2H), 9.53 (broad s, 2H), 11.5 (broad s, 1H), $^{13}$C NMR (75 MHz, DMSO) δ 22.7, 24.1, 44.5, 48.8, 50.1, 53.0, 108.2, 119.1, 125.3, 127.7, 42.1, 146.5, 156.7, 158.3; ES MS(M+1) 286.99; HRMS Calcd. For $C_{16}H_{19}N_3O_2$, 285.34. Found (M+1) 286.15.

Example 37

1-Benzyl-3-hydroxy-4-[4-(2-methoxyphenyl) piperazin-1-ylmethyl]-1H-pyridin-2-one $^1$H NMR (300 MHz, DMSO) δ 2.95 (m, 2H), 3.30 (m, 2H), 3.48 (m, 4H), 3.80 (s, 3H), 4.25 (s, 2H), 5.18 (s, 2H), 6.34 (d, J=7.2 Hz, 1H), 6.93 (m, 2H), 7.01 (m, 2H), 7.34 (m, 6H); $^{19}$F NMR (252 MHz, DMSO) δ 88.5; 13C NMR (75 MHz, DMSO) δ 47.2, 51.8, 53.0, 55.3, 108.1, 112.2, 114.8, 116.2, 118.6, 121.2, 123.8, 127.8, 128.0, 128.9, 137.3, 139.6, 147.5, 152.2, 157.6; ES MS(M+1) 405.82; HRMS Calcd. For $C_{24}H_{27}N_3O_3$, 405.49. Found (M+1) 406.21.

Example 38

1-Benzyl-3-hydroxy-4-[(1-phenylethyl-R-amino) methyl]-1H-pyridin-2-one $^1$H NMR (300 MHz, DMSO) δ 1.58 (d, J=6.9 Hz, 3H), 3.74 (m, 2H), 4.44 (m, 1H), 5.14 (s, 2H), 6.23 (d, J=7.2 Hz, 1H), 7.35 (m, 6H); $^{19}$F NMR (252 MHz, DMSO) δ 89.4; $^{13}$C NMR (75 MHz, DMSO) δ 19.6, 42.6, 51.7, 58.0, 106.9, 18.7, 128.0, 128.1, 128.8, 129.3, 129.4, 137.2, 137.4, 145.9, 157.5; ES MS(M+1) 335.13; Anal. Calcd. For $C_{21}H_{22}N_2O_2$, 334.41. Found (M+1) 335.31.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound of formula (I)

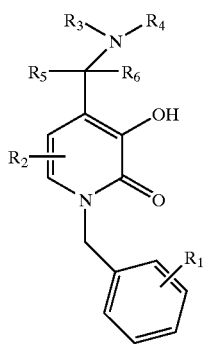

wherein:

a) each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;

b) each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;

c) $R^3$ and $R^4$ are each independently chosen from hydrogen, alkyl, alkenyl, alkynyl, heteroalkyl, aryl, heteroaryl, cycloalkyl, alkylheteroalkyl, alkylaryl, alkylheteroaryl, and alkylcycloalkyl; or $R^3$ and $R^4$, together with the Nitrogen atom to which they are bonded, join to form heteroaryl, or heterocycloalkyl moieties, optionally substituted with one more hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, spirocyloalkyl and combinations thereof;

d) $R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;

e) or optical isomers, diastereomers and enantiomers of the formula above, and pharmaceutically-acceptable salts, biohydrolyzable amides, esters, and imides thereof.

2. The compound of claim 1, wherein each $R^2$ is hydrogen.

3. The compound of claim 1 or claim 2, wherein $R^5$ and $R^6$ are hydrogen.

4. The compound of claim 1, chosen from:

1-Benzyl-3-Hydroxy-4-piperidin-1-ylmethyl-1H-pyridin-2-one;

1-Benzyl-3-Hydroxy-4-morpholin-1-ylmethyl-1H-pyridin-2-one;

1-Benzyl-3-Hydroxy-4-thiamorpholin-1-ylmethyl-1H-pyridin-2-one;

1-Benzyl-3-Hydroxy-4-thiazolidin-1-ylmethyl-1H-pyridin-2-one;

1-Benzyl-4-(benzylaminomethyl)-3-hydroxy-1H-pyridin-2-one;

1-Benzyl-3-Hydroxy-4-[(2-pyridin-2-ylethylamino) methyl]-1H-pyridin-2-one;
1-Benzyl-3-Hydroxy-4-pyrrolidin-1-ylmethyl-1H-pyridin-2-one;
1-Benzyl-4-(4-benzylpiperdin-1-ylmethyl)-3-hydroxy-1H-pyridin-2-one;
1-Benzyl-4-(4-benzylpiperazine-1-ylmethyl)-3-hydroxy-1H-pyrdin-2-one;
1-Benzyl-3-Hydroxy-4-(3-hydroxypyrrolidin-1-ylmethyl)-1H-pyrdin-2-one;
1-Benzyl-3-hydroxy-4-[(2-methoxyethylamino)methyl]-1H-pyridin-2-one;
4Azepan-1-ylmethyl-1-benzyl-3-hydroxy-1H-pyridin-2-one;
4-Azocan-1-ylmethyl-1-benzyl-3-hydroxy-1H-pyrdin-2-one
1-Benzyl-4-(3,4-dihydro-2H-quinolin-1-ylmethyl)-3-hydroxy-1H-pyridin-2-one;
1-(1-Benzyl-3-hydroxy-2-dihydropyridin-4-ylmethyl) pyrrohidine-2-carboxylic acid methyl ester
1-Benzyl-3-hydroxy-4-[(2-hydroxy-1,1-dimethylethylamino)methyl]-1H-pyridin-2-one;
1-Benzyl-3-hydroxy-4-{[(pyridin-4-ylmethyl)amino] methyl}-1H-pyridin-2-one;
1-Benzyl-3-hydroxy-4-(2-methoxymethylpyrrolidin-1-ylmethyl)-1H-Pyrdin-2-one;
1-Benzyl-4-{[(furan-2-ylmethyl)amino]methyl}-3-hydroxy-1H-pyrdin-2-one;
1-Benzyl-3-hydroxy-4-[(2-methylsulfanylethylamino) methyl]-1H-pyridin-2-one;
1-Benzyl-3-hydroxy-4-(2-pyrdin-2-ylpyrrolidin-1-ylmethyl)-1H-pyridin-2-one;
1-Benzyl-3-hydroxy-4-[(4-methoxybenzylamino) methyl]-1H-pyridin-2-one;
1-Benzyl-3-hydroxy-4-[(1-phenylethylamino)methyl]-1H-pyridin-2-one;
1-Benzyl-4-[4-(6-chloropyridazin-3-yl)piperazin-1-ylmethyl]-3-hydroxy-1H-pyridin-2-one;
1-Benzyl-3-hydroxy-4-[(3-imidazol-1-ylpropylamino) methyl]-1H-pyridin-2-one;
1-Benzyl-4-cycloheptylaminomethyl-3-hydroxy-1H-pyrdin-2-one;
1-Benzyl-3-hydroxy-4-[(4-methylcyclohexylamino) methyl]-1H-pyridin-2-one;
3-Hydroxy-1-(3-methoxybenzyl)-4-pyrrolidin-1-ylmethyl-1H-pyridin-2-one;
3-Hydroxy-1-pyridin-4-ylmethyl-4-pyrrolidin-1-ylmethyl-1H-pyridin-2-one;
1-Benzyl-3-hydroxy-4-[4-(2-methoxyphenyl)piperazin-1-ylmethyl]-1H-pyridin-2-one; and
1-Benzyl-3-hydroxy-4-[(1-phenylethyl-R-amino) methyl]-1H-pyridin-2-one5.

5. A method of treating a microbial infection comprising administering a safe and effective of amount of a compound according to claim 1 in a subject in need thereof.

6. A pharmaceutical composition comprising:
  a. a safe and effective of amount of a compound according to claim 1
  b. a pharmaceutically-acceptable excipient.

* * * * *

UNITED STATES PATENT AND TRADEMARK OFFICE
CERTIFICATE OF CORRECTION

PATENT NO.         : 6,930,117 B2
APPLICATION NO. : 10/702953
DATED                  : November 6, 2003
INVENTOR(S)        : Warshakoon et al.

It is certified that error appears in the above-identified patent and that said Letters Patent is hereby corrected as shown below:

Column 15, line 9 of the issued patent, delete " " " after the word Eudragit and insert -- ® --.
    Column 16, line 61 of the issued patent, delete "(6H)" and insert --(m, 6H)--
    Column 22, line 49 of the issued patent, delete

"

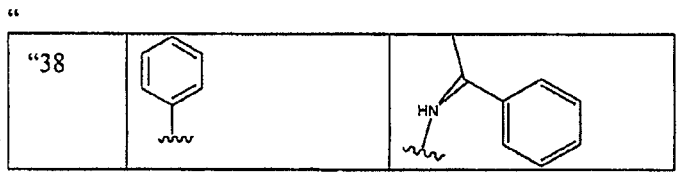

"

and insert --

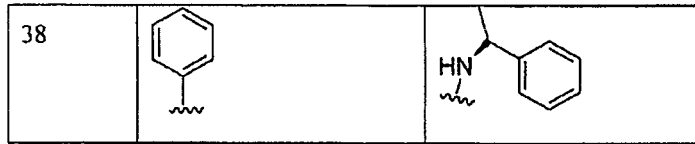

--.

Column 24, line 41 of the issued patent, delete "1-Benzyl-4-[([1,3]-dioxolan-2-ylmethylmethylamino)methyl]-3-hydroxy-1H-pyridin-2-one" and insert --1-Benzyl-4-[([1,3] dioxolan-2-ylmethylmethylamino)methyl]-3-hydroxy-1H-pyridin-2-one--.

Column 25, line 12 of the issued patent, delete "(broad s, 1H)$^{19}$F NMR" and insert --(broad 1H) $^{19}$F NMR--
    Column 25, line 63 of the issued patent, delete "$^{19}$FNMR" and insert --$^{19}$F NMR--.
    Column 27, line 6 of the issued patent, delete "(m, 1H)" and insert –(m,. 1H)--.
    Column 28, line 24 of the issued patent, delete "4-((1-(4-methoxyphenyl)ethylamino)methyl-1-benzyl-3-hydroxypyridin-2(1H)-one" and insert --o)methyl-1-benzyl-3-hydroxypryidin-2(1H)-one--.
    Column 28, line 26 of the issued patent, delete "0.29" and insert --.29--.
    Column 30, lines 1-51, Claim 1 of the issued patent, delete

UNITED STATES PATENT AND TRADEMARK OFFICE
CERTIFICATE OF CORRECTION

| | |
|---|---|
| PATENT NO. | : 6,930,117 B2 |
| APPLICATION NO. | : 10/702953 |
| DATED | : November 6, 2003 |
| INVENTOR(S) | : Warshakoon et al. |

It is certified that error appears in the above-identified patent and that said Letters Patent is hereby corrected as shown below:

Column 30, lines 1-51, Claim 1 of the issued patent, delete

"1.  A compound of formula (I)

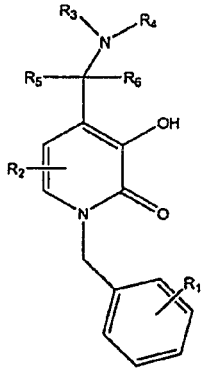

(I)
wherein:

a) each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
b) each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
c) $R^3$ and $R^4$ are each independently chosen from hydrogen, alkyl, alkenyl, alkynyl, heteroalkyl, aryl, heteroaryl, cycloalkyl, alkylheteroalkyl, alkylaryl, alkylheteroaryl, and alkylcycloalkyl; or $R^3$ and $R^4$, together with the Nitrogen atom to which they are bonded, join to form heteroaryl, or heterocycloalkyl moieties, optionally substituted with one more hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, spirocyloalkyl and combinations thereof;
d) $R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
e) or optical isomers, diastereomers and enantiomers of the formula above, and pharmaceutically- acceptable salts, biohydrolyzable amides, esters, and imides thereof."

UNITED STATES PATENT AND TRADEMARK OFFICE
CERTIFICATE OF CORRECTION

PATENT NO. : 6,930,117 B2
APPLICATION NO. : 10/702953
DATED : November 6, 2003
INVENTOR(S) : Warshakoon et al.

It is certified that error appears in the above-identified patent and that said Letters Patent is hereby corrected as shown below:

and insert
--1. A compound of formula (I)

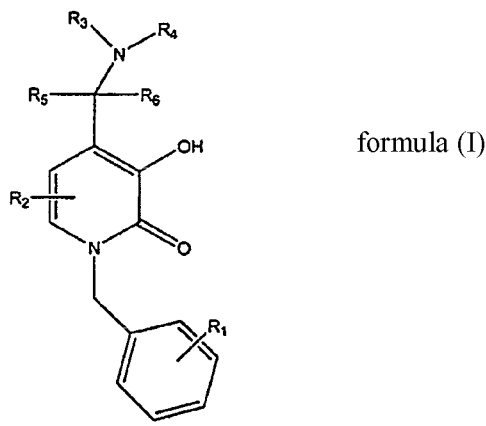

(I)
wherein:
a) each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
b) each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
c) $R^3$ and $R^4$ are each independently chosen from hydrogen, alkyl, alkenyl, alkynyl, heteroalkyl, aryl, cycloalkyl, alkylheteroalkyl, alkylaryl, and alkylcycloalkyl;
d) $R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
e) or optical isomers, diastereomers and enantiomers of the formula above, and pharmaceutically-acceptable salts thereof.--.

Column 30, lines 57 to Column 31 and 32, lines 1-23, Claim 4 of the issued patent, delete:
"4. The compound of claim 1, chosen from:

UNITED STATES PATENT AND TRADEMARK OFFICE
CERTIFICATE OF CORRECTION

PATENT NO. : 6,930,117 B2
APPLICATION NO. : 10/702953
DATED : November 6, 2003
INVENTOR(S) : Warshakoon et al.

It is certified that error appears in the above-identified patent and that said Letters Patent is hereby corrected as shown below:

1-Benzyl-3-Hydroxy-4-piperidin-1-ylmethyl-*1H*-pyridin-2-one;
1-Benzyl-3-Hydroxy-4-morpholin-1-ylmethyl-*1H*-pyridin-2-one;
1-Benzyl-3-Hydroxy-4-thiamorpholin-1-ylmethyl-*1H*-pyridin-2-one;
1-Benzyl-3-Hydroxy-4-thiazolidin- lylmethyl-*1H*-pyridin-2-one;
1-Benzyl-4-(benzylaminomethyl)-3-hydroxy-*1H*-pyridin-2-one;
1-Benzyl-3-Hydroxy-4-[(2-pyridin-2-ylethylamino)methyl]-*1H*-pyridin-2-one;
1-Benzyl-3-Hydroxy-4-pyrrolidin-1-ylmethyl-*1H*-pyridin-2-one;
1-Benzyl-4-(4-benzylpiperdin-1-ylmethyl)-3-hydroxy-*1H*-pyridin-2-one;
1-Benzyl--4-(4-benzylpiperazine-1-ylmethyl)-3-hydroxy-*1H*-pyrdin-2-one;
1-Benzyl-3-Hydroxy-4-(3-hydroxypyrrolidin-1-ylmethyl)-*1H*-pyrdin-2-one
1-Benzyl-3-hydroxy-4-[(2-methoxyethylamino)methyl]-*1H*-pyridin-2-one;
4-Azepan-1-ylmethyl-1-benzyl-3-hydroxy-*1H*-pyridin-2-one;
4-Azocan-1-ylmethyl-1-benzyl-3-hydroxy-*1H*-pyrdin-2-one
1-Benzyl-4-(3,4-dihydro-2H-quinolin-1-ylmethyl)-3-hydroxy-*1H*-pyridin-2-one;
1-(1-Benzyl-3-hydroxy-2-dihydropyridin-4-ylmethyl)pyrrohidine-2-carboxylic acid methyl ester
1-Benzyl-3-hydroxy-4-[(2-hydroxy-1,1-dimethylethylamino)methyl]-*1H*-pyridin-2-one;
1-Benzyl-3-hydroxy-4-{[(pyridin-4-ylmethyl)amino]methyl}-*1H*-pyridin-2-one;
1-Benzyl-3-hydroxy-4-(2-methoxymethylpyrrolidin-1-ylmethyl)-*1H*-Pyrdin-2-one;
1-Benzyl-4-{[(furan-2-ylmethyl)amino)methyl}-3-hydroxy-*1H*-pyrdin-2-one;
1-Benzyl-3-hydroxy-4-[(2-methylsulfanylethylamino)methyl]-*1H*-pyridin-2-one;
1-Benzyl-3-hydroxy-4-(2-pyrdin-2-ylpyrrolidin- 1 -ylmethyl).*1H*-pyridin-2-one;
1-Benzyl-3-hydroxy-4-[(4-methoxybenzylamino)methyl]-*1H*-pyridin-2-one;
1-Benzyl-3-hydroxy-4-[(1-phenylethylamino)methyl]-*1H*-pyridin-2-one;
1-Benzyl-4-[4-(6-chloropyridazin-3-yl)piperazin-1-ylmethyl]-3-hydroxy-*1H*-pyridin-2-one;
1-Benzyl-3-hydroxy-4-[(3-imidazol-1-ylpropylamino)methyl]-*1H*-pyridin-2-one;
1-Benzyl-4-cycloheptylaminomethyl-3-hydroxy-*1H*-pyrdin-2-one;
1-Benzyl-3-hydroxy-4-[(4-methylcyclohexylamino)methyl]-*1H*-pyridin-2-one;
3-Hydroxy-1-(3-methoxybenzyl)-4-pyrrolidin-1-ylmethyl-*1H*-pyridin-2-one;
3-Hydroxy-1-pyridin-4-ylmethyl-4-pyrrolidin-1-ylmethyl-*1H*-pyridin-2-one;
1-Benzyl-3-hydroxy-4-[4-(2-methoxyphenyl)piperazin-1-ylmethyl]-*1H*-pyridin-2-one;
1-Benzyl-3-hydroxy-4-[( 1 -phenylethyl-R-amino)methyl]-*1H*-pyridin-2-one5;"

and insert:
-- 4. The compound of claim 1, chosen from:
1-Benzyl-4-(benzylaminomethyl)-3-hydroxy-*1H*-pyridin-2-one;
1-Benzyl-3-hydroxy-4-[(2-methoxyethylamino)methyl]-*1H*-pyridin-2-one;
1-Benzyl-3-hydroxy-4-[(2-hydroxy-1,1-dimethylethylamino)methyl]-*1H*-pyridin-2-

UNITED STATES PATENT AND TRADEMARK OFFICE
CERTIFICATE OF CORRECTION

PATENT NO. : 6,930,117 B2
APPLICATION NO. : 10/702953
DATED : November 6, 2003
INVENTOR(S) : Warshakoon et al.

It is certified that error appears in the above-identified patent and that said Letters Patent is hereby corrected as shown below:

one;
1-Benzyl-3-hydroxy-4-[(2-methylsulfanylethylamino)methyl]-*1H*-pyridin-2-one;
1-Benzy1-3-hydroxy-4-[(4-methoxybenzylamino)methyl]-*1H*-pyridin-2-one;
4-((1-(4-methoxyphenyl)ethylamino)methyl)-1-benzyl-3-hydroxypyridin-2(1H)-one
1-Benzyl-4-cycloheptylaminomethyl-3-hydroxy-*1H*-pyrdin-2-one; and
1-Benzyl-3-hydroxy-4-[(4-methylcyclohexylamino)methyl]-*1H*-pyridin-2-one.--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO.        : 6,930,117 B2
APPLICATION NO. : 10/702953
DATED             : August 16, 2005
INVENTOR(S)       : Warshakoon et al.

It is certified that error appears in the above-identified patent and that said Letters Patent is hereby corrected as shown below:

Column 15, line 9 of the issued patent, delete " " " after the word Eudragit and insert -- ® --.
    Column 16, line 61 of the issued patent, delete "(6H)" and insert --(m, 6H)--
    Column 22, line 49 of the issued patent, delete

"

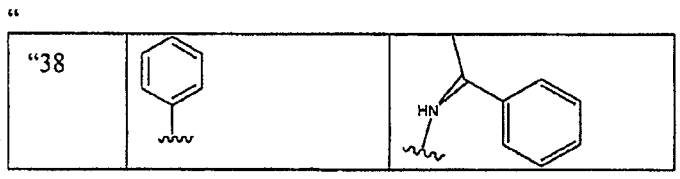

"

and insert --

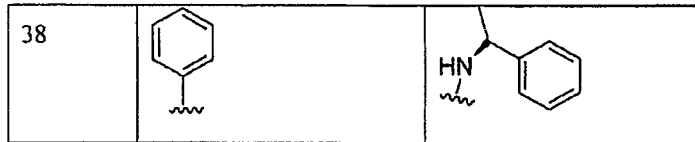

--.

Column 24, line 41 of the issued patent, delete "1-Benzyl-4-[([1,3]-dioxolan-2-ylmethylmethylamino)methyl]-3-hydroxy-1H-pyridin-2-one" and insert --1-Benzyl-4-[([1,3] dioxolan-2-ylmethylmethylamino)methyl]-3-hydroxy-1H-pyridin-2-one--.

Column 25, line 12 of the issued patent, delete "(broad s, 1H)$^{19}$F NMR" and insert --(broad 1H) $^{19}$F NMR--
    Column 25, line 63 of the issued patent, delete "$^{19}$FNMR" and insert --$^{19}$F NMR--.
    Column 27, line 6 of the issued patent, delete "(m, 1H)" and insert –(m,. 1H)--.
    Column 28, line 24 of the issued patent, delete "4-((1-(4-methoxyphenyl) ethylamino)methyl-1-benzyl-3-hydroxypyridin-2(1H)-one" and insert --o)methyl-1-benzyl-3-hydroxypryidin-2(1H)-one--.
    Column 28, line 26 of the issued patent, delete "0.29" and insert --.29--.
    Column 30, lines 1-51, Claim 1 of the issued patent, delete

UNITED STATES PATENT AND TRADEMARK OFFICE
CERTIFICATE OF CORRECTION

PATENT NO.         : 6,930,117 B2
APPLICATION NO. : 10/702953
DATED                 : August 16, 2005
INVENTOR(S)       : Warshakoon et al.

It is certified that error appears in the above-identified patent and that said Letters Patent is hereby corrected as shown below:

Column 30, lines 1-51, Claim 1 of the issued patent, delete

"1.     A compound of formula (I)

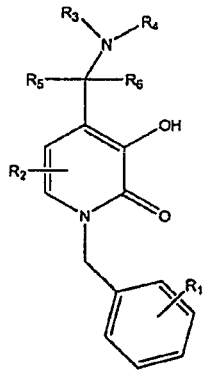

(I)
wherein:

a) each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
b) each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
c) $R^3$ and $R^4$ are each independently chosen from hydrogen, alkyl, alkenyl, alkynyl, heteroalkyl, aryl, heteroaryl, cycloalkyl, alkylheteroalkyl, alkylaryl, alkylheteroaryl, and alkylcycloalkyl; or $R^3$ and $R^4$, together with the Nitrogen atom to which they are bonded, join to form heteroaryl, or heterocycloalkyl moieties, optionally substituted with one more hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, cycloalkyl, spirocyloalkyl and combinations thereof;
d) $R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, heteroaryl, and cycloalkyl;
e) or optical isomers, diastereomers and enantiomers of the formula above, and pharmaceutically- acceptable salts, biohydrolyzable amides, esters, and imides thereof."

UNITED STATES PATENT AND TRADEMARK OFFICE
CERTIFICATE OF CORRECTION

PATENT NO. : 6,930,117 B2
APPLICATION NO. : 10/702953
DATED : August 16, 2005
INVENTOR(S) : Warshakoon et al.

It is certified that error appears in the above-identified patent and that said Letters Patent is hereby corrected as shown below:

and insert
--1. A compound of formula (I)

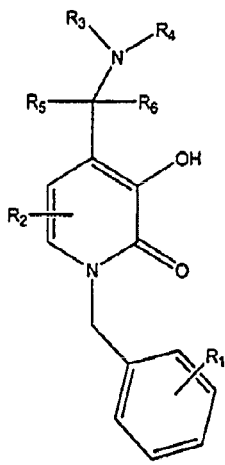

(I)
wherein:
a) each $R^1$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
b) each $R^2$ is independently chosen from hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
c) $R^3$ and $R^4$ are each independently chosen from hydrogen, alkyl, alkenyl, alkynyl, heteroalkyl, aryl, cycloalkyl, alkylheteroalkyl, alkylaryl, and alkylcycloalkyl;
d) $R^5$ and $R^6$ are each independently chosen from of hydrogen, halo, cyano, hydroxy, carboxy, keto, thioketo, amino, acylamino, acyl, amido, phenyl, aryloxy, alkyl, alkenyl, alkynyl, heteroalkyl, halo, haloalkyl, alkoxy, aryl, and cycloalkyl;
e) or optical isomers, diastereomers and enantiomers of the formula above, and pharmaceutically-acceptable salts thereof.--.

Column 30, lines 57 to Column 31 and 32, lines 1-23, Claim 4 of the issued patent, delete:
"4. The compound of claim 1, chosen from:

UNITED STATES PATENT AND TRADEMARK OFFICE
CERTIFICATE OF CORRECTION

PATENT NO. : 6,930,117 B2
APPLICATION NO. : 10/702953
DATED : August 16, 2005
INVENTOR(S) : Warshakoon et al.

It is certified that error appears in the above-identified patent and that said Letters Patent is hereby corrected as shown below:

1-Benzyl-3-Hydroxy-4-piperidin-1-ylmethyl-*1H*-pyridin-2-one;
1-Benzyl-3-Hydroxy-4-morpholin-1-ylmethyl-*1H*-pyridin-2-one;
1-Benzyl-3-Hydroxy-4-thiamorpholin-1-ylmethyl-*1H*-pyridin-2-one;
1-Benzyl-3-Hydroxy-4-thiazolidin- lylmethyl-*1H*-pyridin-2-one;
1-Benzyl-4-(benzylaminomethyl)-3-hydroxy-*1H*-pyridin-2-one;
1-Benzyl-3-Hydroxy-4-[(2-pyridin-2-ylethylamino)methyl]-*1H*-pyridin-2-one;
1-Benzyl-3-Hydroxy-4-pyrrolidin-1-ylmethyl-*1H*-pyridin-2-one;
1-Benzyl-4-(4-benzylpiperdin-1-ylmethyl)-3-hydroxy-*1H*-pyridin-2-one;
1-Benzyl--4-(4-benzylpiperazine-1-ylmethyl)-3-hydroxy-*1H*-pyrdin-2-one;
1-Benzyl-3-Hydroxy-4-(3-hydroxypyrrolidin-1-ylmethyl)-*1H*-pyrdin-2-one
1-Benzyl-3-hydroxy-4-[(2-methoxyethylamino)methyl]-*1H*-pyridin-2-one;
4-Azepan-1-ylmethyl-1-benzyl-3-hydroxy-*1H*-pyridin-2-one;
4-Azocan-1-ylmethyl-1-benzyl-3-hydroxy-*1H*-pyrdin-2-one
1-Benzyl-4-(3,4-dihydro-2H-quinolin-1-ylmethyl)-3-hydroxy-*1H*-pyridin-2-one;
1-(1-Benzyl-3-hydroxy-2-dihydropyridin-4-ylmethyl)pyrrohidine-2-carboxylic acid methyl ester
1-Benzyl-3-hydroxy-4-[(2-hydroxy-1,1-dimethylethylamino)methyl]-*1H*-pyridin-2-one;
1-Benzyl-3-hydroxy-4-{[(pyridin-4-ylmethyl)amino]methyl}-*1H*-pyridin-2-one;
1-Benzyl-3-hydroxy-4-(2-methoxymethylpyrrolidin-1-ylmethyl)-*1H*-Pyrdin-2-one;
1-Benzyl-4-{[(furan-2-ylmethyl)amino)methyl}-3-hydroxy-*1H*-pyrdin-2-one;
1-Benzyl-3-hydroxy-4-[(2-methylsulfanylethylamino)methyl]-*1H*-pyridin-2-one;
1-Benzyl-3-hydroxy-4-(2-pyrdin-2-ylpyrrolidin- 1 -ylmethyl).*1H*-pyridin-2-one;
1-Benzyl-3-hydroxy-4-[(4-methoxybenzylamino)methyl]-*1H*-pyridin-2-one;
1-Benzyl-3-hydroxy-4-[(1-phenylethylamino)methyl]-*1H*-pyridin-2-one;
1-Benzyl-4-[4-(6-chloropyridazin-3-yl)piperazin-1-ylmethyl]-3-hydroxy-*1H*-pyridin-2-one;
1-Benzyl-3-hydroxy-4-[(3-imidazol-1-ylpropylamino)methyl]-*1H*-pyridin-2-one;
1-Benzyl-4-cycloheptylaminomethyl-3-hydroxy-*1H*-pyrdin-2-one;
1-Benzyl-3-hydroxy-4-[(4-methylcyclohexylamino)methyl]-*1H*-pyridin-2-one;
3-Hydroxy-1-(3-methoxybenzyl)-4-pyrrolidin-1-ylmethyl-*1H*-pyridin-2-one;
3-Hydroxy-1-pyridin-4-ylmethyl-4-pyrrolidin-1-ylmethyl-*1H*-pyridin-2-one;
1-Benzyl-3-hydroxy-4-[4-(2-methoxyphenyl)piperazin-1-ylmethyl]-*1H*-pyridin-2-one;
1-Benzyl-3-hydroxy-4-[( 1 -phenylethyl-R-amino)methyl]-*1H*-pyridin-2-one5;"

and insert:
-- 4. The compound of claim 1, chosen from:
1-Benzyl-4-(benzylaminomethyl)-3-hydroxy-*1H*-pyridin-2-one;
1-Benzyl-3-hydroxy-4-[(2-methoxyethylamino)methyl]-*1H*-pyridin-2-one;
1-Benzyl-3-hydroxy-4-[(2-hydroxy-1,1-dimethylethylamino)methyl]-*1H*-pyridin-2-one;

UNITED STATES PATENT AND TRADEMARK OFFICE
CERTIFICATE OF CORRECTION

PATENT NO. : 6,930,117 B2
APPLICATION NO. : 10/702953
DATED : August 16, 2005
INVENTOR(S) : Warshakoon et al.

It is certified that error appears in the above-identified patent and that said Letters Patent is hereby corrected as shown below:

1-Benzyl-3-hydroxy-4-[(2-methylsulfanylethylamino)methyl]-*1H*-pyridin-2-one;
1-Benzyl-3-hydroxy-4-[(4-methoxybenzylamino)methyl]-*1H*-pyridin-2-one;
4-((1-(4-methoxyphenyl)ethylamino)methyl)-1-benzyl-3-hydroxypyridin-2(1H)-one
1-Benzyl-4-cycloheptylaminomethyl-3-hydroxy-*1H*-pyrdin-2-one; and
1-Benzyl-3-hydroxy-4-[(4-methylcyclohexylamino)methyl]-*1H*-pyridin-2-one.--.

This certificate supersedes Certificate of Correction issued November 28, 2006.

Signed and Sealed this

Second Day of January, 2007

JON W. DUDAS
*Director of the United States Patent and Trademark Office*